United States Patent
Gunde et al.

(10) Patent No.: US 11,365,240 B2
(45) Date of Patent: *Jun. 21, 2022

(54) ANTI-HSA ANTIBODIES

(71) Applicant: Numab Therapeutics AG, Wädenswil (CH)

(72) Inventors: Tea Gunde, Zurich (CH); Sebastian Meyer, Eggenwil (CH); Christian Hess, Zurich (CH); Tessa Bieri, Morges (CH)

(73) Assignee: Numab Therapeutics AG, Wädenswil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/618,864

(22) PCT Filed: Jun. 4, 2018

(86) PCT No.: PCT/EP2018/064622
§ 371 (c)(1),
(2) Date: Dec. 3, 2019

(87) PCT Pub. No.: WO2018/224439
PCT Pub. Date: Dec. 13, 2018

(65) Prior Publication Data
US 2020/0325214 A1    Oct. 15, 2020

Related U.S. Application Data

(60) Provisional application No. 62/515,293, filed on Jun. 5, 2017.

(30) Foreign Application Priority Data

Oct. 10, 2017 (EP) ..................... 17195783

(51) Int. Cl.
*C07K 16/18* (2006.01)
(52) U.S. Cl.
CPC .......... *C07K 16/18* (2013.01); *C07K 2317/24* (2013.01); *C07K 2317/31* (2013.01); *C07K 2317/33* (2013.01); *C07K 2317/622* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 2015/0196663 A1* | 7/2015 | Shusta | A61K 9/0085 424/178.1 |
| 2015/0266947 A1* | 9/2015 | Sierks | G01N 33/6896 424/135.1 |

FOREIGN PATENT DOCUMENTS

| WO | 2010/035012 A1 | 4/2010 |
| WO | 2010/094722 A2 | 8/2010 |
| WO | 2010/094723 A2 | 8/2010 |
| WO | 2011/036460 A1 | 3/2011 |
| WO | 2013/068571 A1 | 5/2013 |
| WO | 2014/206561 A1 | 12/2014 |
| WO | 2016/202457 A1 | 12/2016 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
International Search Report and Written Opinion, International Application No. PCT/EP2018/064622 (published under No. 2018/224439), 17 pages (dated Jul. 25, 2018).
Davëet al., "Fab-dsFv: A bispecific antibody format with extended serum half-life through albumin binding," MABS, vol. 8, No. 7, pp. 1319-1335 (Aug. 17, 2016).
Egan et al., "Novel multispecific heterodimeric antibody format allowing modular assembly of variable domain fragments," MABS, vol. 9, No. 1, pp. 68-84 (Oct. 27, 2016).
Schroter et al., "A generic approach to engineer antibody pH-switches using combinatorial histidine scanning libraries and yeast display," MABS, vol. 7, No. 1, pp. 138-151 (Dec. 18, 2014).

* cited by examiner

*Primary Examiner* — Adam Weidner
(74) *Attorney, Agent, or Firm* — Prismatic Law Group, PLLC; Ron Kamis

(57) ABSTRACT

The present invention relates to novel antibodies that are specific for human serum albumin (HSA).

12 Claims, 3 Drawing Sheets
Specification includes a Sequence Listing.

ANTI-HSA ANTIBODIES

CROSS-REFERENCE TO RELATED APPLICATIONS

This application is a 371 national phase of International Patent Application No. PCT/EP2018/064622 filed Jun. 4, 2018, which claims priority to U.S. Provisional Patent Application No. 62/515,293 filed Jun. 5, 2017, and European Patent Application No. 17195783.0 filed Oct. 10, 2017, the content of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN12NP_seqlist2.txt", which was created on Jan. 6, 2022, which is 8,838 bytes in size, and which is herein incorporated by reference in its entirety.

FIELD OF THE INVENTION

The present invention relates to novel antibodies that are specific for human serum albumin (HSA).

BACKGROUND OF THE INVENTION

This invention relates to a novel antibody with binding specificity for human serum albumin, which has advantageous properties, such as high stability, reduced aggregation propensity, and improved binding affinity, and which is particularly suitable for the generation of multispecific antibody constructs.

In the past forty years since the development of the first monoclonal antibodies ("mAbs"; Köhler & Milstein, Nature, 256 (1975) 495-7), antibodies have become an increasingly important class of biomolecules for research, diagnostic and therapeutic purposes. Initially, antibodies were exclusively obtained by immunizing animals with the corresponding antigen of interest. While antibodies of non-human origin can be used in research and diagnostics, in therapeutic approaches the human body may recognize non-human antibodies as foreign and raise an immune response against the non-human antibody drug substance, rendering it less or not effective. Thus, recombinant methods have been set up to render non-human antibodies less immunogenic.

With any chosen approach the resulting mAb or functional fragment ideally retains the desired pharmacodynamic properties of the donor mAb, while displaying drug-like biophysical properties and minimal immunogenicity.

With respect to the biophysical properties of functional fragments of antibodies, the shorter half-life in plasma, when compared to full IgG antibodies, has been a major concern for the developability of therapeutic molecules.

Several approaches have been developed in the past in order to extend the half-life of antibody fragments. These approaches include the use of specific slow release formulations (Mainardes and Silva, 2004), the reduction of the susceptibility of the fragments to serum proteases (Werle and Bernkop-Schnürch, 2006), or the reduction of the intrinsic rate of clearance of the antibody fragments by amino acid substitutions that reduce receptor binding affinity in intracellular endosomal compartments, thereby leading to increased recycling in the ligand-sorting process and consequently resulting in longer half-life in extracellular medium (Sarkar et al., 2002).

In addition, the conjugation of a therapeutic protein to a second molecule that has an inherently long serum half-life has been performed in different settings. One such method is to increase the hydrodynamic size of the protein by chemical attachment of polyethylene glycol (PEG) (Chapman, 2002; Pockros et al., 2004; Veronese and Pasut, 2005), which can produce a drug with a terminal half-life in humans of up to 14 days (Choy et al., 2002), or to conformationally disordered polypeptide sequences composed of the amino acids Pro, Ala, and/or Ser ("PASylation"; see Binder & Skerra (2017) Curr. Opin. Colloid Int. 31 (2017) 10-17). Alternatively, therapeutic proteins have been produced as a genetic fusion with a natural protein that has a long serum half-life; either 67 kDa serum albumin (SA) (Syed et al., 1997; Osborn et al., 2002) or the Fc portion of an antibody, which adds an additional 60-70 kDa in its natural dimeric form, depending on glycosylation (Mohler et al., 1993). This yields drugs that have terminal half-lives in humans of several days (e.g. 4 days for TNF receptor (p75) fused to an Fc region (Lee et al., 2003)).

Holt et al. have extended the latter approach by using anti-serum albumin domain antibodies for extending the half-lives of short lived drugs (Holt et al., Protein Engineering, Design and Selection 21 (2008) 283-288). It could be shown that fusions of such drug with an anti-HSA VH domain antibody resulted in an extension of serum half-life of the interleukin-1 receptor antagonist (IL-1ra). However, Holt et al. exclusively used single domain antibodies, thus limiting use of such technology for approaches based on the interaction of complementary VL and VH domains as heteroassociation domains.

While the use of an anti-HSA antibody or fragment thereof appeared to offer an interesting option, any such antibody would have to exhibit a complex pattern of features in order to successfully address the open issues such an approach poses: (i) the anti-HSA antibody or fragment thereof would have to have a high affinity for HSA; (ii) the anti-HSA antibody or fragment thereof would have to have a high affinity at pH values of about 5.5 and about 7.4 in order to safeguard stable binding at the physiologically relevant conditions; (iii) the antibody has to be specific for HSA, but offer cross-reactivity to non-human primate and/or rodent serum albumin in order to enable the performance of appropriate pre-clinical testing of constructs comprising such anti-HSA antibody or fragment thereof; (iv) binding of the anti-HSA antibody or fragment thereof to HSA has to preserve the ability of the antibody-bound HSA to bind FcRn to allow the anti-HSA antibody or fragment thereof to be recycled with HSA through the interaction between HSA and FcRn; (v) when used in an antibody fragment format, the fragment has to be stable as evidenced by a high melting temperature in thermal unfolding; and (vi) when used in an antibody fragment format, the fragment has to be stable as evidenced by the absence of, or limited amount of, degradation products and/or aggregates in a stress stability study. While it is well known to anyone of skill in the art that it is possible to obtain an antibody having a desired parameter, such as the affinity of an antibody, either by immunization, by library screening or selection and/or by optimization of such parameter of a parental antibody, with a reasonable expectation of success, it is rather unpredictable whether or not it will be possible to obtain or generate an antibody characterized by such a complex pattern of parameters (i) to (vi).

Thus, despite that fact that many attempts have already been made to address the issue of increasing the serum half-life of antibody fragment-based constructs, there still remains a large unmet need to develop novel approaches and/or constructs that can be used in the construction of multispecific antibody constructs and that result in an extension of the half-life of such constructs.

The solution for this problem that has been provided by the present invention, i.e. novel anti-HSA antibodies and fragments thereof, has so far not been achieved or suggested by the prior art.

SUMMARY OF THE INVENTION

The present invention relates to novel antibodies that are specific for human serum albumin (HSA).

Thus, in a first aspect, the present invention relates to an antibody or functional fragment thereof which is specific for human serum albumin, comprising: a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 90% sequence identity to the corresponding LCDRs taken from a VL sequence according to SEQ ID NO: 1 or SEQ ID NO: 3; and
a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 90% sequence identity to the corresponding HCDRs taken from a VH sequence according to SEQ ID NO: 2 or SEQ ID NO: 4.

In a second aspect, the present invention relates to a pharmaceutical composition comprising the antibody or functional fragment thereof of the present invention, and optionally a pharmaceutically acceptable carrier and/or excipient.

In a third aspect, the present invention relates to a nucleic acid sequence or a collection of nucleic acid sequences encoding the antibody or functional fragment thereof of the present invention.

In a fourth aspect, the present invention relates to a vector or a collection of vectors comprising the nucleic acid sequence or the collection of nucleic acid sequences of the present invention.

In a fifth aspect, the present invention relates to a host cell, particularly an expression host cell, comprising the nucleic acid sequence or the collection of nucleic acid sequences of the present invention, or the vector or collection of vectors of the present invention.

In a sixth aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In a seventh aspect, the present invention relates to a method of generating a multispecific construct, comprising the step of cloning, in one or more steps, one or more nucleic acid sequences encoding the antibody or functional fragment thereof according to the present invention, into a multispecific construct comprising at least a second bioactive domain, and, optionally, one or more additional bioactive domains.

In an eighth aspect, the present invention relates to a multispecific polypeptide construct comprising (i) an antibody or functional fragment thereof according to any one of claims 1 to 4; and (ii) a second bioactive domain; and, optionally, (iii) one or more additional bioactive domains.

In a ninth aspect, the present invention relates to the antibody or functional fragment thereof of the present invention, or to a multispecific polypeptide construct comprising the antibody or functional fragment thereof of the present invention for use as a medicament.

In a tenth aspect, the present invention relates to the use of the antibody or functional fragment thereof of the present invention, or a multispecific polypeptide construct comprising the antibody or functional fragment thereof of the present invention in the manufacture of a medicament.

In an eleventh aspect, the present invention relates to a method of treating a subject suffering from a disease, particularly a human disease, comprising administering to said subject an effective amount of the antibody or functional fragment thereof of the present invention or a multispecific polypeptide construct comprising the antibody or functional fragment thereof of the present invention.

In a twelfth aspect, the present invention relates to use of the antibody or functional fragment thereof of the present invention, or to a multispecific polypeptide construct comprising the antibody or functional fragment thereof of the present invention in the treatment of a disease, particularly a human disease.

DETAILED DESCRIPTION OF THE INVENTION

Figure 1:
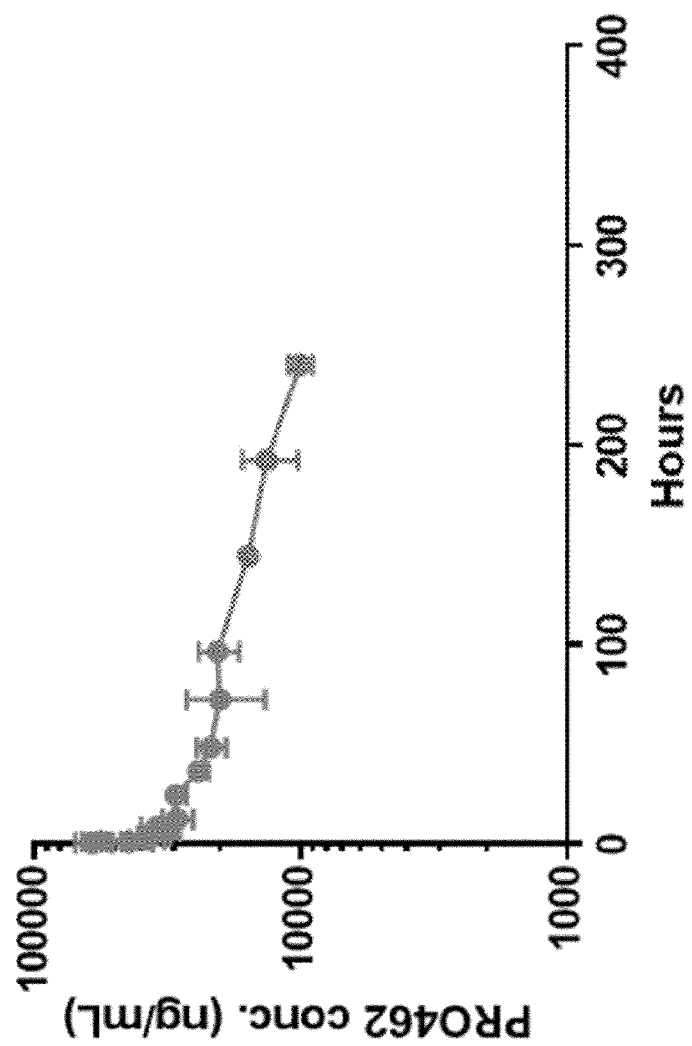
FIG. 1 shows pharmacodynamic parameters of PRO462 following intravenous administration (3 mg/ml) to cynomolgus monkeys (3 per group, average shown; data see Table 8, Example 7). Blood samples were taken over a period of 21 days. The graph shows the mean group plasma concentrations of PRO462. Later time points are omitted because of the development of anti-drug antibodies.

The present disclosure relates to novel antibodies that are specific for human serum albumin (HSA).

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

The term "HSA" refers in particular to human serum albumin with UniProt ID number P02768, or a variant thereof. Human Serum Albumin (HSA) is a 66.4 kDa abundant protein in human serum (50% of total protein) comprised of 585 amino acids (Sugio, Protein Eng, Vol. 12, 1999, 439-446). Multifunctional HSA protein is associated with a structure that allowed to bind and transport a number of metabolites such as fatty acids, metal ions, bilirubin and some drugs (Fanali, Molecular Aspects of Medicine, Vol. 33, 2012, 209-290). HSA concentration in serum is around 3.5-5 g/dL. Albumin-binding antibodies and fragments thereof may be used, for example, for extending the in vivo serum half-life of drugs or proteins conjugated thereto.

Thus, in a first aspect, the present invention relates to an antibody or functional fragment thereof which is specific for human serum albumin, comprising: a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 90% sequence identity to the corresponding LCDRs taken from a VL sequence according to SEQ ID NO: 1 or SEQ ID NO: 3; and a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 90% sequence identity to the corresponding HCDRs taken from a VH sequence according to SEQ ID NO: 2 or SEQ ID NO: 4.

In the context of the present invention, the term "antibody" is used as a synonym for "immunoglobulin" (Ig), which is defined as a protein belonging to the class IgG, IgM, IgE, IgA, IgY or IgD (or any subclass thereof), and includes all conventionally known antibodies. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FWs). Each VH and VL is composed of three CDRs and four FWs arranged from amino-terminus to carboxy-terminus in the following order: FW1-CDR1-FW2-CDR2-FW3-CDR3-FW4. The variable regions of the heavy and light chains contain a binding domain that interacts with an antigen.

The term "antibody fragment" refers to at least one portion of an intact antibody, or recombinant variants thereof, and the term "functional fragment" or "functional antibody fragment" refers an antibody fragment comprising at least an antigen binding domain, e.g., an antigenic determining variable region of an intact antibody, that is sufficient to confer recognition and specific binding of the functional antibody fragment to a target, such as an antigen. Examples of functional antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide bridge at the hinge region, or two or more, e.g., two, isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies). An "antigen-binding region" or "antigen-binding domain" of an antibody typically is found in one or more hypervariable region(s) of an antibody, i.e., the CDR1, CDR2, and/or CDR3 regions; however, the variable "framework" regions can also play an important role in antigen binding, such as by providing a scaffold for the CDRs. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Plückthun ("AHo numbering") is used (Honegger & Plückthun, J. Mol. Biol. 309 (2001) 657-670), unless specifically mentioned otherwise, Furthermore, the following residues are defined as CDRs: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138.

Preferably, the "antigen-binding region" comprises at least amino acid residues 4 to 138 of the variable light (VL) chain and 5 to 138 of the variable heavy (VH) chain (in each case numbering according to Honegger & Plückthun), more preferably amino acid residues 3 to 144 of VL and 4 to 144 of VH, and particularly preferred are the complete VL and VH chains (amino acid positions 1 to 149 of VL and 1 to 149 of VH). The framework regions and CDRs are indicated in Table 2. A preferred class of immunoglobulins for use in the present invention is IgG. "Functional fragments" of the invention include the domain of a F(ab')$_2$ fragment, a Fab fragment, Fv and scFv. The F(ab')$_2$ or Fab may be engineered to minimize or completely remove the intermolecular disulphide interactions that occur between the CH1 and CL domains. The antibodies or functional fragments thereof of the present invention may be part of bi- or multifunctional constructs, as further described in Sections [0079] to [0082].

As used herein, a binding molecule is "specific to/for", "specifically recognizes", or "specifically binds to" a target, such as for example human serum albumin, when such binding molecule is able to discriminate between such target biomolecule and one or more reference molecule(s), since binding specificity is not an absolute, but a relative property. In its most general form (and when no defined reference is mentioned), "specific binding" is referring to the ability of the binding molecule to discriminate between the target biomolecule of interest and an unrelated biomolecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference biomolecule, but a set of about three to five unrelated biomolecules, such as milk powder, transferrin or the like.

However, "specific binding" also may refer to the ability of a binding molecule to discriminate between the target biomolecule and one or more closely related biomolecule(s), which are used as reference points, such as, for example, serum albumins from a different species, e.g. bovine serum albumin. Additionally, "specific binding" may relate to the ability of a binding molecule to discriminate between different parts of its target antigen, e.g. different domains, regions or epitopes of the target biomolecule, or between one or more key amino acid residues or stretches of amino acid residues of the target biomolecule.

In the context of the present invention, the term "epitope" refers to that part of a given target biomolecule that is required for specific binding between the target biomolecule and a binding molecule. An epitope may be continuous, i.e. formed by adjacent structural elements present in the target biomolecule, or discontinuous, i.e. formed by structural elements that are at different positions in the primary sequence of the target biomolecule, such as in the amino acid sequence of a protein as target, but in close proximity in the three-dimensional structure, which the target biomolecule adopts, such as in the bodily fluid.

In a particular embodiment, said variable light chain is a Vκ1 light chain, and/or said variable heavy chain is a VH3 chain. In another particular embodiment, said variable light chain is a chimeric light chain, comprising Vκ framework regions I to III and a Vλ framework region IV. In one embodiment, light chain is a chimeric light chain, comprising:
  (i) CDR domains CDR1, CDR2 and CDR3 taken from a VL sequence according to SEQ ID NO: 1 or SEQ ID NO: 3;
  (ii) human Vκ framework regions FW1 to FW3, particularly human Vκ1 framework regions FW1 to FW3;
  (iii) FW4, which is selected from (a) a human Vλ germ line sequence for FW4, particularly a Vλ germ line sequence selected from the SEQ ID NO: 6 and SEQ ID NO: 7, preferably SEQ ID NO: 7; and (b) a Vλ-based sequence, which has one or two mutations, particularly one mutation, compared to the closest human Vλ germ line sequence for FW4 comprising an amino acid sequence selected from the SEQ ID NO: 6 and SEQ ID NO: 7, preferably SEQ ID NO: 7.

In the context of the present invention the terms "VH" (variable heavy chain), "Vκ" and "Vλ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline κ chain V and J segments, germline λ chain V and J segments, and heavy chain V, D and J segments, respectively. To which subfamily a given antibody variable chain belongs is determined by the corresponding V segment, and in particular by the framework regions FW1 to FW3. Thus, any VH sequence that is characterized in the present application by a particular set of framework regions HFW1 to HFW3 only, may be combined with any HFW4 sequence, for example a HFW4 sequence taken from one of the heavy chain germline J segments, or a HFW4 sequence taken from a rearranged VH sequence. In particular embodiments, the HFW4 sequence is WGQGTLVTVSS.

Suitably, the antibody or functional fragment of the present invention is an isolated antibody or functional fragment thereof. The term "isolated antibody", as used herein, means a polypeptide or a protein thereof which, by virtue of its origin or manipulation: (i) is present in a host cell as the expression product of a portion of an expression vector, or (ii) is linked to a protein or other chemical moiety other than that to which it is linked in nature, or (iii) does not occur in nature. By "isolated" it is further meant a protein that is: (i) chemically synthesized; or (ii) expressed in a host cell and purified away from associated proteins, as by gel chromatography. The term "isolated antibody" also refers to antibody that is substantially free of other antibodies having different antigenic specificities (e.g., an isolated antibody that specifically binds to human serum albumin is substantially free of antibodies that specifically bind antigens other than human serum albumin). An isolated antibody that specifically binds human serum albumin may, however, have cross-reactivity to other antigens, such as serum albumin molecules from other species (e.g., non-human primate and/or rodent serum albumin). Moreover, an isolated antibody may be substantially free of other cellular material and/or chemicals.

"Affinity" refers to the strength of the sum of total noncovalent interactions between a single binding site or a molecule, e.g., an antibody or a functional fragment thereof, and its binding partner, e.g., an antigen. Unless indicated otherwise, as used herein, "binding affinity" refers to intrinsic binding affinity which reflects 1:1 interaction between members of a binding pair, e.g., interaction of a single antibody binding domain and its antigen. The affinity can generally be represented by the dissociation constant ($K_D$). Affinity can be measured by common methods known in the art, including those described herein, in particular affinity can be measured by surface plasmon resonance. In a particular embodiment, the antibody of the invention or the functional fragment may have a $K_D$ of between 1 to 50,000 pM, 1 to 40,000 pM, 1 to 30,000 pM, 1 to 25,000 pM, 1 to 20,000 pM, 1 to 10,000 pM, 1 to 7,500 pM, 1 to 5,000 pM, 1 to 4,000 pM, 1 to 3,000 pM, 1 to 2,000 pM, 1 to 1,500 pM, 1 to 1,000 pM, preferably as measured by surface plasmon resonance; more particularly as determined by the method shown in Example 2.1. In a particular embodiment, the antibody of the invention or the functional fragment thereof has a $K_D$ value for the binding to human serum albumin of less than 50 nM, particularly less than 3 nM, more particularly less than 1 nM, preferably as measured by surface plasmon resonance; more particularly as determined by the method shown in Example 2.1. In a further embodiment, the antibody of the invention or the functional fragment has such $K_D$ value for the binding to human serum albumin both at pH values of about 5.5 and at about 7.4. In a particular embodiment, the antibody of the invention or the functional fragment may have a KD value for the binding to non-human primate and/or rodent serum albumin of between 1 to 250,000 pM, 1 to 200,000 pM, 1 to 150,000 pM, 1 to 100,000 pM, 1 to 75,000 pM, 1 to 50,000 pM, 1 to 40,000 pM, 1 to 30,000 pM, 1 to 20,000 pM, 1 to 10,000 pM, 1 to 7,500 pM, 1 to 5,000 pM, preferably as measured by surface plasmon resonance; more particularly as determined by the method shown in Example 2.1. In a particular embodiment, the antibody of the invention or the functional fragment has a $K_D$ value for the binding to non-human primate and/or rodent serum albumin of less than 250 nM, particularly less than 100 nM, more particularly less than 50 nM, in particular as measured by surface plasmon resonance; more particularly as determined by the method shown in Example 2.1.

In a particular embodiment, said variable light chain exhibits at least 60, 70, 80, 90, 91, 92, 93, 94, 95, 96, 97, 98 or 99 percent, preferably at least 90 percent, sequence identity to a VL sequence according to SEQ ID NO: 1 or SEQ ID NO: 3, and/or wherein said variable heavy chain is a VH3 chain exhibiting at least 60, 70, 80, 90, 91, 92, 93, 94, 95, 96, 97, 98 or 99 percent, preferably at least 90 percent, sequence identity to a VH sequence according to SEQ ID NO: 2 or SEQ ID NO: 4.

The following terms are used to describe the sequence relationships between two or more polynucleotide or amino acid sequences: "sequence identity" or "percentage of sequence identity", and "sequence similarity" or "percentage of sequence similarity". The term "sequence identity" as used herein is determined by calculating the maximum number of amino acid residues that are identical between two polypeptide sequences, wherein gaps and/or insertions may be factored in order to allow for the largest degree of sequence overlap. For example, two 100mer polypeptides that are fully identical have a sequence identity of 100%. When they differ by a single mutation, or when one polypeptide contains a deletion of one amino acid, the sequence identity is 99% (99 out of 100 positions being identical). In other words, the "percentage of sequence identity" is calculated by comparing two optimally aligned sequences over the window of comparison, determining the number of positions at which the identical nucleic acid base (e.g., A, T, C, G, U or I) or amino acid residue occurs in both sequences to yield the number of matched positions, dividing the number of matched positions by the total number of positions in the comparison window (i.e., the window size), and multiplying the result by 100 to yield the percentage of sequence identity. The "sequence similarity" is the degree of resemblance between two sequences when they are compared. Where necessary or desired, optimal alignment of sequences for comparison can be conducted, for example, by the local homology algorithm of Smith and Waterman (Adv. Appl. Math. 2:482 (1981)), by the homology alignment algorithm of Needleman and Wunsch (J. Mol. Biol. 48:443-53 (1970)), by the search for similarity method of Pearson and Lipman (Proc. Natl. Acad. Sci. USA 85:2444-48 (1988)), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)). Unless indicated otherwise herein, the degree of sequence similarity referred to herein is determined by utilization of Dayhoff PAM matrix (M. O. Dayhoff, R. Schwartz, B. C. Orcutt: A model of Evolutionary Change in Proteins, pages 345-352; in: Atlas of protein sequence and structure, National Biomedical Research Foundation, 1979).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

In a particular embodiment, said antibody or functional fragment thereof comprises (i) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 1, and a VH chain exhibiting at least 60, 70, 80, 90, 91, 92, 93, 94, 95, 96, 97, 98 or 99 percent, preferably at least 90 percent, sequence identity to the VH sequence according to SEQ ID NO: 2, or (ii) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 3, and a VH chain exhibiting at least 60, 70, 80, 90, 91, 92, 93, 94, 95, 96, 97, 98 or 99 percent, preferably at least 90 percent, sequence identity to the VH sequence according to SEQ ID NO: 4.

In one embodiment, the present invention relates to an antibody or functional fragment thereof which is specific for human serum albumin, comprising: (i) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 1, wherein said variable light chain comprises CDR domains CDR1, CDR2 and CDR3 taken from a the VL sequence according to SEQ ID NO: 1; and (ii) a variable heavy chain exhibiting at least 60, 70, 80, 90, 91, 92, 93, 94, 95, 96, 97, 98 or 99 percent, preferably at least 90 percent, sequence identity to the VH sequence according to SEQ ID NO: 2, wherein said variable heavy chain comprises CDR domains CDR1, CDR2 and CDR3 taken from a the VH sequence according to SEQ ID NO: 2. In a more specific embodiment, the present invention relates to an antibody or functional fragment thereof which is specific for human serum albumin, comprising: (i) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 1, wherein said variable light chain comprises CDR domains CDR1, CDR2 and CDR3 taken from a the VL sequence according to SEQ ID NO: 1, and wherein said variable light chain comprises K50Q and A51P (AHo numbering); and (ii) a variable heavy chain exhibiting at least 60, 70, 80, 90, 91, 92, 93, 94, 95, 96, 97, 98 or 99 percent, preferably at least 90 percent, sequence identity to the VH sequence according to SEQ ID NO: 2, wherein said variable heavy chain comprises CDR domains CDR1, CDR2 and CDR3 taken from the VH sequence according to SEQ ID NO: 2, and wherein said variable heavy chain comprises W54Y, V103T and Y105F (AHo numbering).

In a specific embodiment, the present invention relates to an antibody or functional fragment thereof which is specific for human serum albumin, comprising (i) a variable light chain comprising the amino acid sequence according to SEQ ID NO: 1 or a conservatively modified variant thereof, and (ii) a variable heavy chain comprising the amino acid sequence according to SEQ ID NO: 2 or a conservatively modified variant thereof. In a more specific embodiment, the present invention relates to an antibody or functional fragment thereof which is specific for human serum albumin, comprising (i) a variable light chain comprising the amino acid sequence according to SEQ ID NO: 1, and (ii) a variable heavy chain comprising the amino acid sequence according to SEQ ID NO: 2.

In one embodiment, the present invention relates to an antibody or functional fragment thereof which is specific for human serum albumin, comprising: (i) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 3, wherein said variable light chain comprises CDR domains CDR1, CDR2 and CDR3 taken from the VL sequence according to SEQ ID NO: 3; and (ii) a variable heavy chain exhibiting at least 60, 70, 80, 90, 91, 92, 93, 94, 95, 96, 97, 98 or 99 percent, preferably at least 90 percent, sequence identity to the VH sequence according to SEQ ID NO: 4, wherein said variable heavy chain comprises CDR domains CDR1, CDR2 and CDR3 taken from the VH sequence according to SEQ ID NO: 4. In a more specific embodiment, the present invention relates to an antibody or functional fragment thereof which is specific for human serum albumin, comprising: (i) a variable light chain exhibiting at least 60, 70, 80, 90, 91, 92, 93, 94, 95, 96, 97, 98 or 99 percent, preferably at least 90 percent, sequence identity to the VL sequence according to SEQ ID NO: 3, wherein said variable light chain comprises CDR domains CDR1, CDR2 and CDR3 taken from the VL sequence according to SEQ ID NO: 3, and wherein said variable light chain comprises I2V, Q3V, K50Q and A51P (AHo numbering); and (ii) a variable heavy chain exhibiting at least 60, 70, 80, 90, 91, 92, 93, 94, 95, 96, 97, 98 or 99 percent, preferably at least 90 percent, sequence identity to the VH sequence according to SEQ ID NO: 4, wherein said variable heavy chain comprises CDR domains CDR1, CDR2 and CDR3 taken from the VH sequence according to SEQ ID NO: 4, and wherein said variable heavy chain comprises I55V, V103T, Y105F (AHo numbering).

In a specific embodiment, the present invention relates to an antibody or functional fragment thereof which is specific for human serum albumin, comprising (i) a variable light chain comprising the amino acid sequence according to SEQ ID NO: 3 or a conservatively modified variant thereof, and (ii) a variable heavy chain comprising the amino acid sequence according to SEQ ID NO: 4 or a conservatively modified variant thereof. In a more specific embodiment, the present invention relates to an antibody or functional fragment thereof which is specific for human serum albumin, comprising (i) a variable light chain comprising the amino acid sequence according to SEQ ID NO: 3, and (ii) a variable heavy chain comprising the amino acid sequence according to SEQ ID NO: 4.

The term "conservatively modified variant" or "conservative variants" applies to both amino acid and nucleic acid sequences. With respect to particular nucleic acid sequences, conservatively modified variants refer to those nucleic acids, which encode identical or essentially identical amino acid sequences, or, where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule.

Accordingly, each silent variation of a nucleic acid that encodes a polypeptide is implicit in each described sequence.

For polypeptide sequences, "conservatively modified variants" or "conservative variants" include individual substitutions, deletions or additions to a polypeptide sequence, which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

In particular embodiment, the antibody of the invention or the functional fragment thereof, is characterized by one or more of the following parameters:
(i) it has a $K_D$ value for the binding to human serum albumin of less than 50 nM, particularly less than 3 nM, more particularly less than 1 nM, in particular as measured by surface plasmon resonance; more particularly as determined by the method shown in Example 2.1;
(ii) it has such $K_D$ value for the binding to human serum albumin both at pH values of about 5.5 and at about 7.4, in particular as measured by surface plasmon resonance;
(iii) it has a $K_D$ value for the binding to non-human primate and/or rodent serum albumin of less than 250 nM, particularly less than 100 nM, more particularly less than 50 nM, in particular as measured by surface plasmon resonance; more particularly as determined by the method shown in Example 2.1;
(iv) binding of the anti-HSA antibody or fragment thereof to HSA has to preserve the ability of the antibody-bound HSA to bind FcRn to allow the anti-HSA antibody or fragment thereof to be recycled with HSA through the interaction between HSA and FcRn, as determined by the assay used in Example 2.2;
(v) it has an average midpoint of thermal unfolding temperature (Tm) exceeding at least 60° C., when expressed in the scDb (single chain diabody format) or scFv (single chain variable fragment format) antibody format, preferably when expressed in the scFv format, in particular as determined by differential scanning fluorimetry (DSF) as described earlier (Egan, et al., MAbs, 9(1) (2017), 68-84; Niesen, et al., Nature Protocols, 2(9) (2007) 2212-2221), in particular when samples are diluted in five phosphate-citrate buffers at pH values ranging from 3.5 to 7.5 and containing 0.15-0.25 M NaCl, particularly 0.15 M NaCl. The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in relevant excipient conditions are prepared at a final protein concentration of 50 µg ml$^{-1}$ by spiking in stock excipients that are prepared in relevant buffer. For a buffer scouting experiment samples are diluted in final scFv buffers with different pH values (pH 3.4, 4.4, 5.4, 6.4 and 7.2) containing a final concentration of 5× SYPRO® Orange in a total volume of 100 µl. Along with the unknown samples the scFv DSF reference is measured as internal control. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve; the reported Tm is an average of three measurements; in a particular embodiment, the determination of Tm is performed as described in Example 4.1, wherein a sample is diluted in phosphate-citrate buffer at a pH value of 6.4, which contains 0.25 M NaCl; and
(vi) when used in an antibody fragment format, the fragment has to be stable as evidenced by the absence of, or limited amount of, degradation products and/or aggregates, as evidenced by less than 3% loss of monomeric content at 37° C. during 28 days in a stress stability study, in particular performed in accordance with Example 4.2, particularly less than 2% loss of monomeric content, in particular when the antibody of the invention is at a starting concentration of 10 mg/ml.

In a preferred embodiment, said antibody or functional fragment thereof has an average midpoint of thermal unfolding temperature (Tm) exceeding at least 65° C., preferably at least 69° C. The protein is analyzed over the course of 14 days of storage at 37° C. in 50 mM citrate-phosphate pH 6.4, 150 mM NaCl with respect to oligomerization by SE-HPLC. Prior to the study the samples are concentrated to 10 g l−1 and d0 time points are determined. The monomer content is quantified by separation of the samples on a Shodex KW-402.5-4F column and evaluation of the resulting chromatograms. For the calculation of the relative percentage of protein monomer the area of the monomeric peak is divided by the total area of peaks that cannot be attributed to the sample matrix. In a preferred embodiment, said antibody or functional fragment thereof exhibits a loss of monomeric content of less than 15%, 12%, 10%, 7%, 5%, or 2% when stored for two weeks at a concentration of 10 g/l at 37° C. in 50 mM Citrate-Phosphate pH 6.4, 150 mM NaCl, preferably less than 5%, more preferably less than 2%.

In one embodiment of the present invention, the isolated antibody or functional fragment thereof is selected from: an IgG antibody, a Fab and an scFv fragment. Suitably, the antibody of the invention or functional fragment thereof is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding. "Single-chain Fv" or "scFv" antibody fragments comprise the VH and VL domains of antibody, wherein these domains are present in a single polypeptide chain. Generally, the scFv polypeptides further comprises a polypeptide linker between the VH and VL domains which enables the scFv to form the desired structure for antigen binding (see, for example, Plückthun, The pharmacology of Monoclonal Antibodies, vol. 113, Rosenburg and Moore eds., Springer-Verlag, New York, 1994, pp. 269-315).

In particular embodiments, said functional fragment is an scFv format comprising the linker according to SEQ ID NO: 5.

In another particular embodiment of the present invention, the isolated antibody or functional fragment thereof is a multispecific construct, e.g., bispecific construct, or a multivalent constructs, e.g., bivalent construct, which is an antibody format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), triabody, scDb-scFv, bispecific Fab2, di-miniantibody, tetrabody, scFv-Fc-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), and Knob-into-Hole antibodies (KiHs) (bispecific IgGs prepared by the KiH technology), a MATCH (described in WO2016/0202457; Egan T., et al., mAbs 9 (2017) 68-84) and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb), in particular a bispecific monomeric scDb. More particularly suitable for use herein is a scDb-scFv or MATCH, preferably scDb-scFv.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. Diabodies may be bivalent or bispecific. Diabodies are described more fully in, for example, EP404097, WO1993/01161, Hudson et al., Nat. Med. 9:129-134 (2003), and Hollinger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. The middle linker L2 particularly is a peptide of 10-40 amino acids, more particularly 15-30 amino acids, and most particularly 20-25 amino acids.

In one embodiment of the present invention, the isolated antibody or functional fragment thereof is a multispecific and/or multivalent antibody in a MATCH format described in WO2016/0202457; Egan T., et al., mAbs 9 (2017) 68-84.

The bispecific, bivalent, multispecific and/or multivalent constructs of the present invention can be produced using any convenient antibody manufacturing method known in the art (see, e.g., Fischer, N. & Leger, O., Pathobiology 74 (2007) 3-14 with regard to the production of bispecific constructs; Hornig, N. & Färber-Schwarz, A., Methods Mol. Biol. 907 (2012) 713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two different monoclonal antibodies to give a bispecific construct using known molecular cloning techniques.

In a second aspect, the present invention relates to a pharmaceutical composition comprising the antibody or functional fragment thereof of the present invention, and optionally a pharmaceutically acceptable carrier and/or excipient.

The phrase "pharmaceutically acceptable" refers to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

Pharmaceutical compositions in accordance with the present disclosure may further routinely contain pharmaceutically acceptable concentrations of salt, buffering agents, preservatives, supplementary immune potentiating agents such as adjuvants and cytokines and optionally other therapeutic agents. The composition may also include antioxidants and/or preservatives. As antioxidants may be mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiaretic acid. Suitable preservatives may for instance be phenol, chlorobutanol, benzylalcohol, methyl paraben, propyl paraben, benzalkonium chloride and cetylpyridinium chloride.

In particular embodiments provided herein, said antibodies or functional fragments thereof can be isolated, prepared, expressed, or created by recombinant means, such as antibodies expressed using a recombinant expression vector transfected into a host cell, antibodies isolated from a recombinant, combinatorial antibody library, or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences.

Thus, in a third aspect, the present invention relates to a nucleic acid sequence or a collection of nucleic acid sequences encoding the antibody or functional fragment thereof of the present invention.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

In a fourth aspect, the present invention relates to a vector or a collection of vectors comprising the nucleic acid sequence or a collection of nucleic acid sequences of the present invention. The term "vector" or "expression vector" means a polynucleotide, most commonly a DNA plasmid, comprising nucleotide sequences encoding the antibodies of the invention or a fragment thereof for recombinant expression in host cells, preferably in mammalian cells. A vector may, or may not, be able to replicate in a cell. Once a polynucleotide encoding variable heavy and/or variable light chain of an antibody, or fragment thereof described herein has been obtained, the vector for the production of the antibody molecule can be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

An expression vector can be transferred to a host cell by conventional techniques and the resulting cells can then be cultured by conventional techniques to produce an antibody described herein or a fragment thereof. Thus, the present invention relates to a host cell, particularly an expression host cell, comprising the nucleic acid sequence or the collection of nucleic acid sequences of the present invention, or the vector or collection of vectors of the present invention. In certain embodiments, a host cell contains a vector comprising a polynucleotide encoding both the variable heavy chain and variable light chain of the antibody of the invention, or a fragment thereof. In specific embodiments, a host cell contains two different vectors, a first vector comprising a polynucleotide encoding a variable heavy chain of said antibody, or a fragment thereof, and a second vector comprising a polynucleotide encoding a variable light chain of said antibody, or a fragment thereof. In other embodiments, a first host cell comprises a first vector comprising a polynucleotide encoding a variable heavy chain of said antibody, or a fragment thereof, and a second host cell comprises a second vector comprising a polynucleotide encoding a variable light chain of said antibody, or a functional fragment thereof.

Methods for the humanization of rabbit antibodies or rodent antibodies are well known to anyone of ordinary skill in the art (see, for example, Borras, loc. cit.; Rader et al, The FASEB Journal, express article 10.1096/fj.02-0281fje, published online Oct. 18, 2002; Yu et al (2010) A Humanized Anti-VEGF Rabbit Monoclonal Antibody Inhibits Angiogenesis and Blocks Tumor Growth in Xenograft Models. PLoS ONE 5(2): e9072. doi:10.1371/journal.pone.0009072). The immunization of the rabbits or rodents may be performed with the antigen of interest as such, such as a protein, or, in the case of peptide or protein antigens, by DNA immunization of a rabbit with a nucleic acid, e.g. a plasmid, encoding the peptides or proteins of interest.

In a fifth aspect, the present invention relates to a host cell, particularly an expression host cell, comprising the nucleic acid sequence or the collection of nucleic acid sequences of the present invention, or the vector or collection of vectors of the present invention.

The term "host cell" refers to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

In a sixth aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In a seventh aspect, the present invention relates to a method of generating a multispecific construct, comprising the step of cloning, in one or more steps, one or more nucleic acid sequences encoding the antibody or functional fragment thereof according to the present invention, into a multispecific construct comprising at least a second bioactive domain, and, optionally, one or more additional bioactive domains.

In an eighth aspect, the present invention relates to a multispecific polypeptide construct comprising (i) an antibody or functional fragment thereof according to the present invention; and (ii) a second bioactive domain; and, optionally, (iii) one or more additional bioactive domains.

In particular embodiments of the seventh or eighth aspect, the second bioactive domain is a second antibody or functional fragment thereof.

In particular embodiments, at least one of said optional, additional bioactive domains is present, particularly wherein said additional bioactive domain is a third antibody or functional fragment thereof.

In particular embodiments, the multispecific polypeptide construct further comprises one or more polypeptide linkers.

In particular embodiments, said multispecific polypeptide is a monomeric polypeptide, particularly a monomeric polypeptide wherein the antibody or functional fragment thereof according to the present invention is an scFv antibody fragment linked via a linker to said second bioactive domain, particularly wherein said second bioactive domain is a second scFv antibody fragment.

In particular embodiments, said multispecific polypeptide is a dimeric polypeptide, particularly a dimeric polypeptide, wherein the association of the two polypeptides is caused by the association of complementary VL and VH domains of antibody fragments comprised in said multispecific polypeptide. In particular such embodiments, the multispecific polypeptide is a multispecific antibody construct in accordance with the teaching of WO 2016/202457. In particular other embodiments, the multispecific polypeptide is a single-chain diabody construct (scDb). In particular other embodiments, the multispecific polypeptide is a Fab-scFv)$_n$ construct (n being an integer selected from 1, 2, 3, or 4) that employs a heterodimeric assembly of a Fab fragment consisting of VL-CL and VH-CH1 with either constant domain forming a scaffold, to which one or more scFv fragments are attached via flexible linkers.

In a ninth aspect, the present invention relates to the antibody or functional fragment thereof of the present invention, or to a multispecific polypeptide construct comprising the antibody or functional fragment thereof of the present invention for use as a medicament. In one embodiment, the present invention relates to a multispecific polypeptide construct comprising the antibody or functional fragment thereof of the present invention for use in the treatment of a disease, particularly a human disease, wherein said multispecific polypeptide construct comprises a second bioactive domain, which is able to specifically interact with a target of therapeutic relevance in the corresponding disease.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, e.g., arresting its development; and (c) relieving the disease, e.g., causing regression of the disease.

In a tenth aspect, present invention relates to the use of the antibody or functional fragment thereof of the present invention, or a multispecific polypeptide construct comprising the antibody or functional fragment thereof of the present invention in the manufacture of a medicament.

In an eleventh aspect, the present invention relates to a method of treating a subject suffering from a disease, particularly a human disease, comprising administering to said subject an effective amount of the antibody or functional fragment thereof of the present invention or a multispecific polypeptide construct comprising the antibody or functional fragment thereof of the present invention. In one embodiment, the present invention relates to a method of treating a subject suffering from a disease, particularly a human disease, comprising administering to said subject an effective amount of a multispecific polypeptide construct comprising the antibody or functional fragment thereof of the present invention, wherein said multispecific polypeptide construct comprises a second bioactive domain, which is able to specifically interact with a target of therapeutic relevance in the corresponding disease.

The term "subject" includes human and non-human animals. Non-human animals include all vertebrates, e.g., mammals and non-mammals, such as non-human primates, sheep, dog, cow, chickens, amphibians, and reptiles. In a preferred embodiment, said subject is human. Except when noted the terms "patient" or "subject" are used herein interchangeably.

The term "effective amount" or "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

In a twelfth aspect, the present invention relates to use of the antibody or functional fragment thereof of the present invention, or to a multispecific polypeptide construct comprising the antibody or functional fragment thereof of the present invention in the treatment of a disease, particularly a human disease, particularly wherein said multispecific polypeptide construct comprises a second bioactive domain, which is able to specifically interact with a target of therapeutic relevance in the corresponding disease.

EXAMPLES

The following examples illustrate the invention without limiting its scope.

Example 1: Selection and Humanization

For the Lead Candidate generation of the HSA binding domain 15 rabbit monoclonal antibody clones were selected.

The humanization of the selected clone comprised the transfer of the rabbit CDRs onto a scFv acceptor framework of the Vκ1/VH3 type comprising a Vλ framework IV sequence as described in WO 2014/206561. In this process the amino acid sequence of the six CDR regions was identified on the donor sequence (rabbit mAb) and grafted into the acceptor scaffold sequence.

Additional amino acids from the rabbit donor in certain framework positions, which have been described to potentially influence CDR positioning and thus antigen binding (Borras et al., 2010; J. Biol. Chem., 285:9054-9066) were included in the final constructs (see Table 1). The comparison of the characterization data for these constructs revealed a significant advantage over the CDR grafting alone. The sequences of the resulting variable domains are shown in Table 2.

Once the in-silico construct design described in the previous section was completed the corresponding genes were synthesized and bacterial expression vectors were constructed. The sequence of the expression constructs was confirmed on the level of the DNA and the constructs were manufactured according to generic expression and purification protocols.

The heterologous expression of the proteins was performed in *E. coli* as insoluble inclusion bodies. The expression culture was inoculated with an exponentially growing starting culture. The cultivation was performed in shake flasks in an orbital shaker using commercially available rich media. The cells were grown to a defined OD600 of 2 and induced by overnight expression with 1 mM Isopropyl β-D-1-thiogalactopyranoside (IPTG). At the end of fermentation the cells were harvested by centrifugation and homogenized by sonication. At this point the expression level of the different constructs was determined by SDS-PAGE analysis of the cell lysate. The inclusion bodies were isolated from the homogenized cell pellet by a centrifugation protocol that included several washing steps to remove cell debris and other host cell impurities. The purified inclusion bodies were solubilized in a denaturing buffer (100 mM Tris/HCl pH 8.0, 6 M Gdn-HCl, 2 mM EDTA) and the scFvs were refolded by a scalable refolding protocol that generated milligram amounts of natively folded, monomeric scFv. A standardized protocol was employed to purify the scFvs, which included the following steps. The product after refolding was captured by an affinity chromatography employing Capto L agarose (GE Healthcare) to yield the purified scFvs. Lead candidates that met the affinity and potency criteria in initial testing were further purified by a polishing size-exclusion chromatography using a HiLoad Superdex75 column (GE Healthcare). Subsequent to the purification protocol the proteins were formulated in a buffered saline solution and characterized.

Example 2: Characterization of Humanized scFvs 2.1 Affinity to Serum Albumin at pH 7.4 and pH 5.5

Affinity of the humanized scFvs to serum albumin (SA) of the different species was determined by SPR measurements using a MASS-1 device (Sierra Sensors). SA was directly coupled to a high capacity amine sensor chip (Sierra Sensors) using amine coupling chemistry. After performing a regeneration scouting and surface performance test to find best assay conditions, a scFv dose response was measured and obtained binding curves were double-referenced (empty reference channel and zero analyte injection) and fitted using the 1:1 Langmuir model to retrieve kinetic parameters. The assay was run twice at different pH values: once in a 1×PBS-Tween buffer at pH 5.5 and another time in a 1×PBS-Tween buffer at pH 7.4.

The measurements of the binding kinetics for the humanized constructs show a difference in cross-species reactivity of the two clones and quantitative differences in the CDR and STR grafts tested. For both construct pairs the incorporation of the described structural residues led to an improvement of affinity. For the constructs of clone 19-01-H04 the improvement of affinity was up to 20 to 300-fold depending on the tested species and pH. For the constructs of clone 23-13-A01 a modest improvement of about 3-fold was achieved (see Table 3).

In terms of cross-species reactivity the clone 19-01-H04 shows high affinity binding to human and non-human primates serum albumin, while no binding was observed for rodent SA. For the clone 23-13-A01 high affinity binding was observed for human and non-human primate SA, in addition the molecules bind with reduced affinity to rodent SA (see Table 4).

2.2 FcRn Binding of Antibody-Bound HSA

An assay was set up at pH 5.5 to confirm that scFv-bound HSA is still capable of binding FcRn. This is necessary to allow the anti-HSA scFv or derivative thereof to be recycled with HSA through the interaction between HSA and FcRn. An assay was developed using an HSA-immobilized chip: 1. 90 nM scFv was injected and the interaction was measured at low pH; 2. 90 nM FcRn was injected and the interaction was measured at low pH 3. A 1:1 mixture of scFv and FcRn (90 nM each) was injected to see whether the sum of the binding levels of the individual injections approximates the binding level when the mixture is injected. If the scFv-bound HSA can no longer bind FcRn the binding level of the mixture would be the same as the binding level of the scFv alone.

By using this assay it could be confirmed that the HSA is fully capable to bind to FcRn when bound by scFvs of the clones 19-01-H04 and 23-13-A01.

Example 3: Generation of a Single-Chain Diabody (scDb) Format

For further characterization of the αHSA domain properties the preferred domains were incorporated into multi-specific constructs.

For both domains bispecific constructs in the single-chain diabody were made. The construct design in the single-chain diabody (scDb) format was performed as described previously [Holliger et al., "Diabodies": small bivalent and bispecific antibody fragments. Proc. Natl. Acad. Sci. U.S.A. 90, 6444-6448]. In short, the variable domains as listed in Table 1 were arranged in an VLA-S1-VHB-L1-VLB-S2-VHA fashion, where S1 and S2 are short $G_4S$ linkers and L1 is a long $(G_4S)_4$ linker. The resulting constructs with the αHSA domains and a second specificity for a second antigen were termed PRO462, in case of the domains 19-01-H04-sc02, and PRO480, in case of the domains 23-13-A01-sc02.

The nucleotide sequences were de novo synthesized and cloned into an adapted vector for E. coli expression that is based on a pET26b(+) backbone (Novagen). The expression construct was transformed into the E. coli strain BL12 (DE3) (Novagen) and the cells were cultivated in 2YT medium (Sambrook, J., et al., Molecular Cloning: A Laboratory Manual) as a starting culture. Expression cultures were inoculated and incubated in shake flasks at 37° C. and 200 rpm. Once an OD600 nm of 1 is reached protein expression was induced by the addition of IPTG at a final concentration of 0.5 mM. After overnight expression the cells were harvested by centrifugation at 4000 g. For the preparation of inclusion bodies the cell pellet was resuspended in IB Resuspension Buffer (50 mM Tris-HCl pH 7.5, 100 mM NaCl, 5 mM EDTA, 0.5% Triton X-100). The cell slurry was supplemented with 1 mM DTT, 0.1 mg/mL Lysozyme, 10 mM Leupeptin, 100 µM PMSF and 1 µM Pepstatin. Cells were lysed by 3 cycles of ultrasonic homogenization while being cooled on ice. Subsequently 0.01 mg/mL DNAse was added and the homogenate was incubated at room temperature for 20 min. The inclusion bodies were sedimented by centrifugation at 15000 g and 4° C. The IBs were resuspended in IB Resuspension Buffer and homogenized by sonication before another centrifugation. In total a minimum of 3 washing steps with IB Resuspension Buffer were performed and subsequently 2 washes with IB Wash Buffer (50 mM Tris-HCl pH 7.5, 100 mM NaCl, 5 mM EDTA) to yield the final IBs.

For protein refolding the isolated IBs were resuspended in Solubilization Buffer (100 mM Tris/HCl pH 8.0, 6 M Gdn-HCl, 2 mM EDTA) in a ratio of 5 mL per g of wet IBs. The solubilization was incubated for 30 min at room temperature until DTT was added at a final concentration of 20 mM and the incubation was continued for another 30 min. After the solubilization was completed the solution was cleared by 10 min centrifugation at 21500 g and 4° C. The refolding was performed by rapid dilution at a final protein concentration of 0.3 g/L of the solubilized protein in Refolding Buffer (typically: 100 mM Tris-HCl pH 8.0, 5.0 M Urea, 5 mM Cysteine, 1 mM Cystine). The refolding reaction was routinely incubated for a minimum of 14 h. The resulting protein solution was cleared by 10 min centrifugation at 8500 g and 4° C. The refolded protein was purified by affinity chromatography on Capto L resin (GE Healthcare). The isolated monomer fraction was analyzed by size-exclusion HPLC, SDS-PAGE for purity and UV/Vis spectroscopy for protein content. Buffer was exchange into Native buffer (50 mM Citrate-Phosphate pH 6.4, 200 mM NaCl) by dialysis. The protein concentrations were adjusted to the intended value for the stability analysis.

Example 4: Functional Characterization of the Single-Chain Diabody (scDb) Constructs 4.1 Thermal Unfolding The midpoint of transition for the thermal unfolding of the tested constructs was determined by Differential Scanning Fluorimetry (DSF), essentially as described by Niesen (Niesen et al., Nat Protoc. 2 (2007) 2212-21). The DSF assay is performed in a qPCR machine (e.g. MX3005p, Agilent Technologies). The samples are diluted in buffer (citrate-phosphate pH 6.4, 0.25 M NaCl) containing a final concentration of 5× SYPRO orange in a total volume of 25 µL. Samples are measured in triplicates and a temperature ramp from 25-96° C. programmed. The fluorescence signal is acquired and the raw data is analyzed with the GraphPad Prism (GraphPad Software Inc.).

Representative data created using constructs closely related to those disclosed in this application are shown in Table 5.

4.2 Stress Stability Study

The protein is analyzed over the course of four weeks and storage at 37° C. with respect to oligomerization by size-exclusion high-performance liquid chromatography (SE-HPLC) and degradation by sodium dodecyl sulfate polyacrylamide gel electrophoresis (SDS-PAGE). Prior to the study the samples are concentrated to 1 and starting time points are determined. The monomer content is quantified by separation of the samples on a Shodex KW-402.5-4F (Showa Denko) and evaluation of the resulting chromatograms. For the calculation of the relative percentage of protein monomer the area of the monomeric peak is divided by the total area of peaks that cannot be attributed to the sample matrix. The protein degradation is assessed by SDS-PAGE analysis with Any kD Mini-Protean TGX gels (Bio-Rad Laboratories) and stained with Coomassie brilliant blue. The protein concentration is monitored at the different time points by UV-Vis spectroscopy with an Infinity reader M200 Pro equipped with a Nanoquant plate (Tecan Group Ltd.).

The stability data of PRO462 and PRO480 in combination with the confirmation of the antigen binding by SPR show the stability and structural integrity of the respective αHSA domains in the context of a multispecific antibody format (see Table 6).

Example 5: Generation of Construct PRO497 (Fab-scFv)$_2$

The Fab-(scFv)$_2$ format is a multifunctional recombinant antibody derivative that employs a heterodimeric assembly of Fab fragments consisting of VL-CL and VH-CH1 with either constant domain forming a scaffold, upon which via flexible linkers additional binding domains, such as scFvs, can be incorporated (Schoonjans, Willems et al. 2001) (Schoonjans, Willems et al. 2000). The molecules can be co-expressed in mammalian host cells such as CHO—S where the binding immunoglobulin chaperon drives heterodimerization of VL-CL and VH-CH1 domains even in presence of chain extensions. These heterodimers are stable, with each of the binders retaining their specific affinities. ScFv fusions at positions CL and CH1 of the Fab-(scFv)$_2$ molecule are considered as equivalent. The only non-natural sequence fragments in the molecule are peptide linkers connecting variable domains within scFv domains and scFv domains with Fab constant domains are composed of glycin-serine-polymers which are considered to be neither antigenic nor immunogenic. PRO497 is a Fab-(scFv)$_2$ molecule comprising an anti-CD3 specific (09-24-H09-sc04) Fab portion with an anti-HSA specific scFv domain (23-13-A01-sc02) fused to the CL domain and an anti-IL23R specific scFv domain (14-11-D07-sc04) fused to the CH1 domain. Domains within scFv domains are connected via 20 amino acid $(G_4S)_4$ linkers while individual scFv domains are fused via 15 amino acid $(G_4S)_3$ peptide linkers to the Fab fragment.

Schoonjans, R., A. Willems, J. Grooten and N. Mertens (2000). "Efficient heterodimerization of recombinant bi- and trispecific antibodies." Bioseparation 9(3): 179-183.

Schoonjans, R., A. Willems, S. Schoonooghe, W. Fiers, J. Grooten and N. Mertens (2000). "Fab chains as an efficient heterodimerization scaffold for the production of recombinant bispecific and trispecific antibody derivatives." J Immunol 165(12): 7050-7057.

Example 6: Functional Characterization of Construct PRO497 by In-Vivo PK Studies Pharmacokinetics of PRO497 in Mice The objective of this study was to determine the pharmacokinetics of PRO497 following intravenous administration to male CD-1 mice. Twelve animals were administered 5 mg/kg of PRO497 by the intravenous route. Blood samples were collected pre-dose, 10 min, 30 min, 1 h, 2 h, 4 h, 8 h, 12 h, 24 h, 48 h, 96 h and 144 h post dose. Following collection whole blood for serum was placed into serum separator tubes and allowed to clot. Samples were observed for the presence of clot retraction and centrifuged [2200×g for 10 minutes at ambient temperature]. Serum samples were transferred to individual polypropylene vials and immediately placed on dry ice before storage at −70±10° C.

Figure 2:
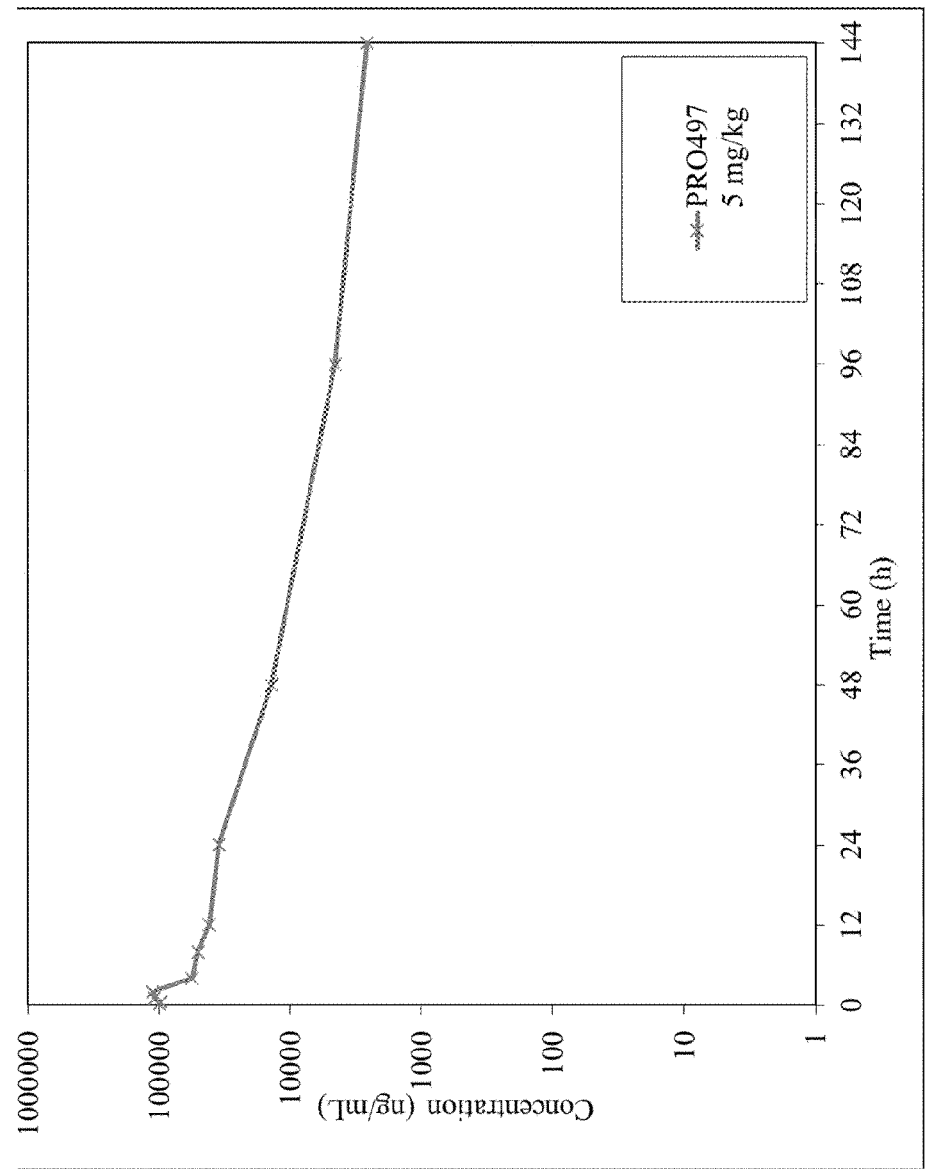
FIG. 2 shows the results of the mouse PK study discussed in Example 6 (mean group plasma concentrations of PRO497 in male CD-1 mice intravenously dosed with 5 mg/kg of test article; data see Table 9).
Figure 3:
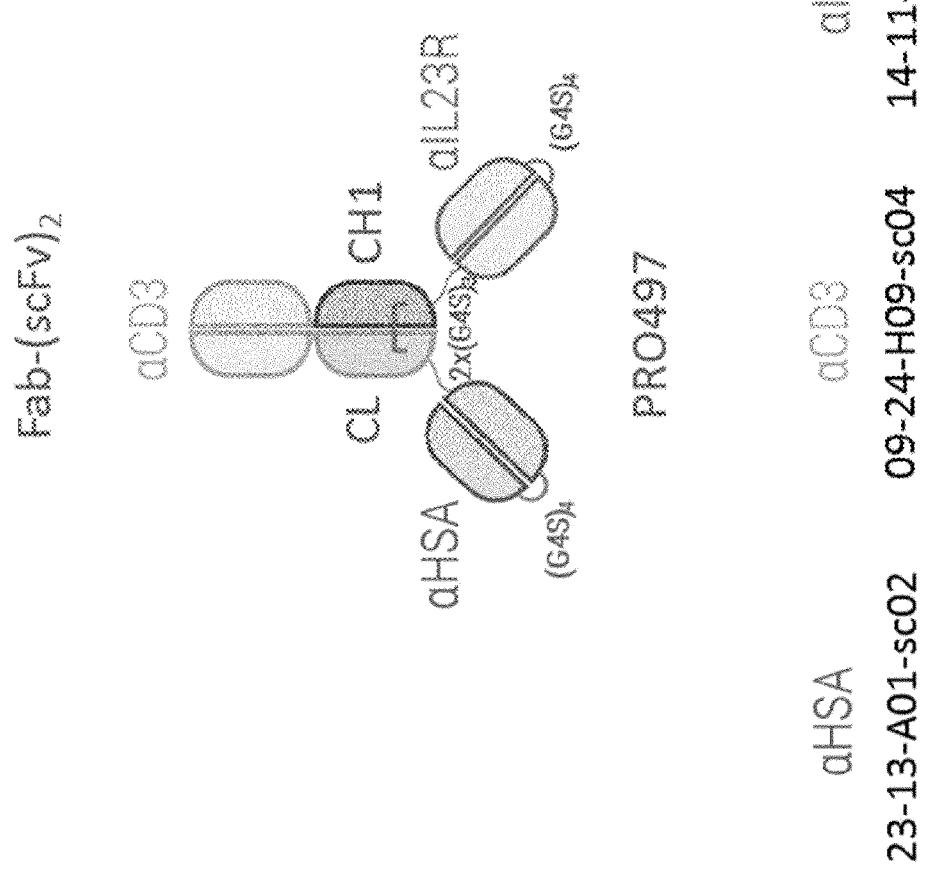
FIG. 3 shows the structure of the multispecific construct PRO497.

Concentrations of PRO497 in serum were analyzed using a quantitative ELISA for detection of PRO479 in mouse serum (FIG. 2). Pharmacokinetic parameters were estimated using Watson pharmacokinetic software (Thermo Electron Corporation, Version No. 7.2.0.02) employing a non-compartmental approach consistent with the intravenous route of administration.

Example 7: Functional Characterization of Construct PRO462 by In-Vivo PK Studies Pharmacokinetics of PRO462 in Cynomolgus Monkey The pharmacokinetics of PRO462 were determined following intravenous administration to male cynomolgus monkeys. A total of three non-naïve animals received a single administration of PRO462 at a target dose level of 3 mg/kg. Serum was prepared from blood samples that were collected at the following timepoints:

Pre-dose, 10 and 30 min and 1, 2, 4, 6, 8, 12, 24, 36, 48, 72, 96, 144, 192, 240, 288, 336, 384, 432 and 504 h post-dose.

Concentrations of PRO462 in serum were analyzed using a quantitative ELISA (FIG. 1). Pharmacokinetic parameters were estimated using WinNonlin pharmacokinetic software (Phoenix version 1.4) using a non-compartmental approach.

TABLE 1

Rabbit residues grafted in addition to the
CDR regions (numbering according to AHo)

| Clone ID | Graft | Structural residues grafted |
|---|---|---|
| 19-01-H04-sc01 | CDR | |
| 19-01-H04-sc02 | STR | VL: (K50Q; A51P) VH: (W54Y; V103T; Y105F) |
| 23-13-A01-sc01 | CDR | |
| 23-13-A01-sc02 | STR | VL: (I2V, Q3V, K50Q, A51P) VH: (I55V, V103T, Y105F) |

TABLE 2

Sequence listing, showing the CDR residues in bold lettering

| Sequence ID (SEQ ID) | Description | Sequence |
|---|---|---|
| 1 | Anti-HSA VL 19-01-H04-sc02 | DIQMTQSPSSLSASVGDRVTITC QSSESVYSNNQLS WYQQKPGQPPKLLIY DASDLAS GVPSRFSGSGSGTDFTLTISSLQPEDFATYYC AGGFSSSSDTA FGGGTKLTVLG |
| 2 | Anti-HSA VH 19-01-H04-sc02 | EVQLVESGGGLVQPGGSLRLSCAAS GFSLSSNAMG WVRQAPGKGLEYIG IISVGGFT YYASWAKG RFTISRDNSKNTVYLQMNSLRAEDTATYFCA RDRHGGDSSGAFYL WG QGTLVTVSS |
| 3 | Anti-HSA VL 23-13-A01-sc02 | DVVMTQSPSSLSASVGDRVTITC QASQIISSRSA WYQQKPGQPPKLLIY QASKLASG VPSRFSGSGSGTDFTLTISSLOPEDFATYYC QCTYIDSNFGA FGGGTKLTVLG |
| 4 | Anti-HSA VH 23-13-A01-sc02 | EVQLVESGGGLVQPGGSLRLSCAAS GFSFSSSYWIC WVRQAPGKGLEWVG CVFTG DGTTYYASWAKG RFTISRDNSKNTVYLQMNSLRAEDTATYFCA RPVSVYYYGMDL W GQGTLVTVSS |
| 5 | Linker | GGGGSGGGGSGGGGSGGGGS |
| 6 | Vλ germline-based FR4 (Sk17) | FGTGTKVTVLG |
| 7 | Vλ germline-based FR4 (Sk12) | FGGGTKLTVLG |

(in SEQ ID NOs: 1 to 4, the CDRs are indicated in bold and italic letters)

TABLE 3

Affinity measurement of humanized scFv constructs derived from clone 19-01-H04 and 23-13-A01. The binding kinetics for human and cynomolgus serum albumin were determined at pH 5.5 and pH 7.4.

| Clone ID | | Affinity for human SA pH 5.5 (SPR) | | | Affinity for human SA pH 7.4 (SPR) | | |
|---|---|---|---|---|---|---|---|
| | | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] |
| 19-01-H04-sc01 | CDR | 1.78E+05 | 2.32E-03 | 1.30E-08 | 1.02E+05 | 3.43E-03 | 3.36E-08 |
| 19-01-H04-sc02 | STR | 4.50E+05 | 3.08E-04 | 6.84E-10 | 3.84E+05 | 4.11E-04 | 1.07E-09 |
| 23-13-A01-sc01 | CDR | 1.14E+05 | 1.24E-04 | 1.09E-09 | 8.21E+04 | 2.11E-04 | 2.57E-09 |
| 23-13-A01-sc02 | STR | 3.07E+05 | 1.15E-04 | 3.73E-10 | 3.23E+05 | 1.94E-04 | 6.00E-10 |

| Clone ID | Affinity for cynomolgus SA pH 5.5 (SPR) | | | Affinity for cynomolgus SA pH 7.4 (SPR) | | |
|---|---|---|---|---|---|---|
| | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] |
| 19-01-H04-sc01 | 1.35E+04 | 1.57E-03 | 1.16E-07 | 1.18E+05 | 2.37E-03 | 2.01E-08 |
| 19-01-H04-sc02 | 5.98E+05 | 2.31E-04 | 3.87E-10 | 4.24E+05 | 3.02E-04 | 7.11E-10 |
| 23-13-A01-sc01 | | | | | | |
| 23-13-A01-sc02 | 3.38E+05 | 2.53E-04 | 7.50E-10 | 3.34E+05 | 4.33E-04 | 1.30E-09 |

TABLE 4

Affinity measurement of humanized scFv constructs derived from clone 19-01-H04 and 23-13-A01. The binding kinetics for mouse and rat serum albumin were determined at pH 5.5 and pH 7.4. Measurements of marmoset serum albumin were made at pH 5.5.

| Clone ID | | Affinity for mouse SA pH 5.5 (SPR) | | | Affinity for mouse SA pH 7.4 (SPR) | | | Affinity for rat SA pH 5.5 (SPR) |
|---|---|---|---|---|---|---|---|---|
| | | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] | $k_a$ [M$^{-1}$ s$^{-1}$] |
| 19-01-H04-sc01 | CDR | | | | | | | |
| 19-01-H04-sc02 | STR | | | | | | | |
| 23-13-A01-sc01 | CDR | 4.85E+04 | 8.63E-04 | 1.78E-08 | | | | 1.20E+05 |
| 23-13-A01-sc02 | STR | 1.92E+05 | 9.33E-04 | 4.86E-09 | 1.46E+05 | 4.69E-03 | 3.22E-08 | 2.34E+05 |

| Clone ID | Affinity for rat SA pH 5.5 (SPR) | | Affinity for rat SA pH 7.4 (SPR) | | | Affinity for marmoset (purified) SA pH 5.5 (SPR) | | |
|---|---|---|---|---|---|---|---|---|
| | $k_d$ [s$^{-1}$] | $K_D$ [M] | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] |
| 19-01-H04-sc01 | | | | | | | | |
| 19-01-H04-sc02 | | | | | | 3.86E+06 | 2.60E-03 | 6.74E-10 |
| 23-13-A01-sc01 | 2.83E-03 | 2.37E-08 | | | | | | |
| 23-13-A01-sc02 | 4.37E-03 | 1.87E-08 | 1.06E+05 | 2.45E-02 | 2.31E-07 | 3.38E+05 | 1.28E-03 | 3.77E-09 |

TABLE 5

Midpoint of unfolding as measured by DSF αHSA containing scDbs

| Protein ID | Melting temperature ° C. |
|---|---|
| PRO462 | 60.6 |
| PRO480 | 60.1 |

TABLE 6

SE-HPLC results of the stability study conducted with PRO462 and PRO480

| Protein ID | Storage Temp. ° C. | Monomeric content % | | | | | | | Monomeric content loss % | | | | | |
|---|---|---|---|---|---|---|---|---|---|---|---|---|---|---|
| | | d0 | d1 | d2 | d7 | d14 | d21 | d28 | d1 | d2 | d7 | d14 | d21 | d28 |
| PRO462 | 4° C. | 100.0 | 100.0 | 99.7 | 99.7 | 99.3 | 99.8 | 99.3 | 0.0 | 0.3 | 0.3 | 0.7 | 0.2 | 0.6 |
| | 37° C. | 100.0 | 99.6 | 96.8 | 99.3 | 98.7 | 98.9 | 98.3 | 0.3 | 3.2 | 0.7 | 1.3 | 1.1 | 1.7 |
| | −80° C. | | | | | | | 99.3 | | | | | | 0.7 |
| PRO480 | 4° C. | 100.0 | 99.9 | 99.3 | 99.6 | 98.5 | 99.7 | 98.5 | 0.1 | 0.7 | 0.4 | 1.5 | 0.3 | 1.5 |
| | 37° C. | 100.0 | 99.2 | 99.7 | 98.8 | 97.9 | 98.3 | 97.6 | 0.8 | 0.3 | 1.1 | 2.1 | 1.6 | 2.3 |
| | −80° C. | | | | | | | 98.7 | | | | | | 1.2 |

TABLE 7

Affinity data measured by SPR for PRO462 and PRO480

| Protein ID | Affinity to human serum albumin pH 5.5 | | | Affinity to human serum albumin pH 7.4 | | |
|---|---|---|---|---|---|---|
| | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] |
| PRO462 | 8.97E+05 | 3.33E-04 | 3.71E-10 | 4.74E+05 | 3.45E-04 | 7.28E-10 |
| PRO480 | 7.50E+04 | 1.73E-04 | 2.30E-09 | 7.01E+04 | 2.35E-04 | 3.36E-09 |

| Protein ID | Affinity to cynomolgus serum albumin pH 5.5 | | | Affinity to cynomolgus serum albumin pH 7.4 | | |
|---|---|---|---|---|---|---|
| | $k_a$ [M$^{-1}$ s$^{-1}$] | $k_d$ [s$^{-1}$] | $K_D$ [M] | $k_a$ [M$^{-1}$ s$^{-1}$] | $k_d$ [s$^{-1}$] | $K_D$ [M] |
| PRO462 | 1.00E+06 | 1.75E-04 | 1.75E-10 | 6.30E+05 | 2.21E-04 | 3.51E-10 |
| PRO480 | 7.76E+04 | 3.73E-04 | 4.82E-09 | 5.70E+04 | 5.49E-04 | 9.63E-09 |

TABLE 8

Data underlying graph shown in FIG. 1

| ID | C0 (ng/ml) | AUC(0-t) (ng · h/mL) | AUC(0-inf) (ng · h/mL) | CL (mL · h/kg) | Vd (mL/kg) | $T_{1/2}$ (h) |
|---|---|---|---|---|---|---|
| PRO462 | 71'200 ± 11'100 | 4'600'000 ± 440'000 | 6'800'000 ± 624'000 | 0.446 ± 0.0468 | 96.0 ± 14.8 | 150 (6.3 days) ± 18.9 (0.8 days) |

TABLE 9

Data underlying graph shown in FIG. 2

| ID | C0 (ng/ml) | AUC(0-t) (ng · h/mL) | AUC(0-inf) (ng · h/mL) | CL (mL · h/kg) | Vd (mL/kg) | $T_{1/2}$ (h) |
|---|---|---|---|---|---|---|
| PRO497 | 100'412 ± 12'159 | 2'350'000 | 2'500'000 | 0.0355 | 70.5 | 39.7 (1.7 days) |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The invention claimed is:

1. An antibody or functional fragment thereof which is specific for human serum albumin, comprising:
   (a) a variable light chain,
      wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs consist of the LCDRs QSSESVYSNNQLS (SEQ ID NO: 11), DASDLAS (SEQ ID NO: 12) and AGGFSSSSDTA (SEQ ID NO: 13);
   and
   a variable heavy chain,
      wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs consist of the HCDRs GFSLSSNAMG (SEQ ID NO: 14), IISVGGFTYYASWAKG (SEQ ID NO: 15) and RDRHGGDSSGAFYL (SEQ ID NO: 16); or
   (b) a variable light chain,
      wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs consist of the LCDRs QASQIISSRSA (SEQ ID NO: 17), QASKLAS SEQ ID NO: 18) and QCTYIDSNFGA (SEQ ID NO: 19); and
   a variable heavy chain,
      wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs consist of the HCDRs GFSFSSSYWIC (SEQ ID NO: 20), CVFTGDGTTYYASWAKG (SEQ ID NO: 21) and RPVSVYYYGMDL (SEQ ID NO: 22).

2. The antibody or functional fragment thereof according to claim 1, wherein said variable light chain is a Vκ1 light chain, and/or wherein said variable heavy chain is a VH3 chain.

3. The antibody or functional fragment thereof according to claim 1, wherein said antibody or functional fragment thereof is characterized by one or more of the following parameters:
   (i) a $K_D$ value for the binding to human serum albumin of less than 50 nM as measured by surface plasmon resonance;
   (ii) a $K_D$ value for the binding to human serum albumin of less than 50 nM as measured by surface plasmon resonance;
   (iii) a $K_D$ value for the binding to non-human primate and/or rodent serum albumin of less than 250 nM as measured by surface plasmon resonance;
   (iv) preserved ability of the antibody-bound HSA to bind to FcRn;
   (v) an average midpoint of thermal unfolding temperature (Tm) exceeding at least 60° C., when expressed in the scDb (single chain diabody format) or scFv (single chain variable fragment format) antibody format as determined by differential scanning fluorimetry, when samples are diluted in citrate-phosphate buffers at pH values ranging from 3.5 to 7.5, and containing 0.15-0.25 M NaCl; and
   (vi) less than 3% loss of monomeric content at 37° C. during 28 days in a stress stability study, when the antibody or functional fragment thereof is at a starting concentration of 10 mg/ml.

4. A pharmaceutical composition comprising the antibody or functional fragment thereof of claim 1, and a pharmaceutically acceptable carrier and/or excipient.

5. A nucleic acid sequence or a collection of nucleic acid sequences encoding the antibody or functional fragment thereof according to claim 1.

6. A vector or a collection of vectors comprising the nucleic acid sequence or the collection of nucleic acid sequences of claim 5 in a vector or a collection of vectors.

7. A method for producing the antibody or functional fragment thereof of claim 1, comprising the step of expressing a nucleic acid sequence or a collection of nucleic acid sequences encoding the antibody or functional fragment thereof, or a vector or collection of vectors encoding said nucleic acid sequence or collection of nucleic acid sequences so that the antibody or functional fragment thereof of claim 1 is produced.

8. A method of generating a multispecific construct, comprising the step of
   (a) cloning, in one or more steps, one or more nucleic acid sequences encoding the antibody or functional fragment thereof according to claim 1 as a first bioactive domain, into a multispecific construct comprising at least a second bioactive domain, and, optionally, one or more additional bioactive domains.

9. The method of claim 8, wherein said second bioactive domain is a second antibody or functional fragment thereof.

10. A multispecific polypeptide construct comprising (i) an antibody or functional fragment thereof according to claim 1; and (ii) a second bioactive domain; and, optionally, (iii) one or more additional bioactive domains.

11. The multispecific polypeptide construct of claim 10, wherein said second bioactive domain is a second antibody or functional fragment thereof.

12. An antibody or functional fragment thereof which is specific for human serum albumin, comprising:
   (a) a variable light chain,
      wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs consist of the LCDRs QSSESVYSNNQLS (SEQ ID NO: 11), DASDLAS (SEQ ID NO: 12) and AGGFSSSSDTA (SEQ ID NO: 13) and wherein the variable light chain has at least 90% sequence identity to the variable light chain sequence according to SEQ ID NO: 1;
   and
   a variable heavy chain,
      wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs consist of the HCDRs GFSLSSNAMG (SEQ ID NO: 14), IISVGGFTYYASWAKG (SEQ ID NO: 15) and RDRHGGDSSGAFYL (SEQ ID NO: 16) and wherein the variable heavy chain has at least 90% sequence identity to the variable heavy chain sequence according to SEQ ID NO: 2; or
   (b) a variable light chain,
      wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs consist of the LCDRs QASQIISSRSA (SEQ ID NO: 17), QASKLAS (SEQ ID NO: 18) and QCTYIDSNFGA (SEQ ID NO: 19) and wherein the variable light chain has at least 90% sequence identity to the variable light chain sequence according to SEQ ID NO: 3;
   and
   a variable heavy chain,
      wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs consist of the HCDRs GFSFSSSYWIC (SEQ ID NO: 20), CVFTGDGTTYYASWAKG (SEQ ID NO: 21) and RPVSVYYYGMDL (SEQ ID NO: 22) and wherein the variable heavy chain has at least 90% sequence identity to the variable heavy chain sequence according to SEQ ID NO: 4.

\* \* \* \* \*

```
                        SEQUENCE LISTING

<160> NUMBER OF SEQ ID NOS: 22

<210> SEQ ID NO 1
<211> LENGTH: 112
<212> TYPE: PRT
<213> ORGANISM: Artificial Sequence
<220> FEATURE:
<223> OTHER INFORMATION: recombinant antibody sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Ser Asn
                20                  25                  30

Asn Gln Leu Ser Trp Tyr Gln Gln Lys Pro Gly Gln Pro Pro Lys Leu
            35                  40                  45

Leu Ile Tyr Asp Ala Ser Asp Leu Ala Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Phe Ser Ser
                85                  90                  95

Ser Ser Asp Thr Ala Phe Gly Gly Gly Thr Lys Leu Thr Val Leu Gly
                100                 105                 110

<210> SEQ ID NO 2
<211> LENGTH: 121
<212> TYPE: PRT
<213> ORGANISM: Artificial Sequence
<220> FEATURE:
<223> OTHER INFORMATION: recombinant antibody sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
                20                  25                  30
```

```
Ala Met Gly Trp Val Arg Gln Ala Pro Gly Lys Gly Leu Glu Tyr Ile
        35                  40                  45

Gly Ile Ile Ser Val Gly Gly Phe Thr Tyr Tyr Ala Ser Trp Ala Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Thr Tyr Phe Cys Ala
                 85                  90                  95

Arg Asp Arg His Gly Gly Asp Ser Ser Gly Ala Phe Tyr Leu Trp Gly
                100                 105                 110

Gln Gly Thr Leu Val Thr Val Ser Ser
            115                 120

<210> SEQ ID NO 3
<211> LENGTH: 110
<212> TYPE: PRT
<213> ORGANISM: Artificial Sequence
<220> FEATURE:
<223> OTHER INFORMATION: recombinant antibody sequence

<400> SEQUENCE: 3

Asp Val Val Met Thr Gln Ser Pro Ser Ser Leu Ser Ala Ser Val Gly
 1               5                  10                  15

Asp Arg Val Thr Ile Thr Cys Gln Ala Ser Gln Ile Ile Ser Ser Arg
                20                  25                  30

Ser Ala Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Cys Thr Tyr Ile Asp Ser Asn
                 85                  90                  95

Phe Gly Ala Phe Gly Gly Gly Thr Lys Leu Thr Val Leu Gly
                100                 105                 110

<210> SEQ ID NO 4
<211> LENGTH: 121
<212> TYPE: PRT
<213> ORGANISM: Artificial Sequence
<220> FEATURE:
<223> OTHER INFORMATION: recombinant antibody sequence

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Ser
                20                  25                  30

Tyr Trp Ile Cys Trp Val Arg Gln Ala Pro Gly Lys Gly Leu Glu Trp
            35                  40                  45

Val Gly Cys Val Phe Thr Gly Asp Gly Thr Thr Tyr Tyr Ala Ser Trp
 50                  55                  60

Ala Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Phe
                 85                  90                  95
```

Cys Ala Arg Pro Val Ser Val Tyr Tyr Gly Met Asp Leu Trp Gly
                100                 105                 110

Gln Gly Thr Leu Val Thr Val Ser Ser
        115                 120

<210> SEQ ID NO 5
<211> LENGTH: 20
<212> TYPE: PRT
<213> ORGANISM: Artificial Sequence
<220> FEATURE:
<223> OTHER INFORMATION: recombinant antibody sequence

<400> SEQUENCE: 5

Gly Gly Gly Gly Ser Gly Gly Gly Gly Ser Gly Gly Gly Gly Ser Gly
1               5                   10                  15

Gly Gly Gly Ser
            20

<210> SEQ ID NO 6
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 6

Phe Gly Thr Gly Thr Lys Val Thr Val Leu Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 7

Phe Gly Gly Gly Thr Lys Leu Thr Val Leu Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 8

Trp Gly Gln Gly Thr Leu Val Thr Val Ser Ser
1               5                   10

<210> SEQ ID NO 9
<211> LENGTH: 5
<212> TYPE: PRT
<213> ORGANISM: Artificial Sequence
<220> FEATURE:
<223> OTHER INFORMATION: recombinant antibody sequence

<400> SEQUENCE: 9

Gly Gly Gly Gly Ser
1               5

<210> SEQ ID NO 10
<211> LENGTH: 15
<212> TYPE: PRT
<213> ORGANISM: Artificial Sequence

```
<220> FEATURE:
<223> OTHER INFORMATION: recombinant antibody sequence

<400> SEQUENCE: 10

Gly Gly Gly Gly Ser Gly Gly Gly Ser Gly Gly Gly Gly Ser
1               5                   10                  15

<210> SEQ ID NO 11
<211> LENGTH: 13
<212> TYPE: PRT
<213> ORGANISM: artificial sequence
<220> FEATURE:
<223> OTHER INFORMATION: recombinant antibody sequence

<400> SEQUENCE: 11

Gln Ser Ser Glu Ser Val Tyr Ser Asn Asn Gln Leu Ser
1               5                   10

<210> SEQ ID NO 12
<211> LENGTH: 7
<212> TYPE: PRT
<213> ORGANISM: artificial sequence
<220> FEATURE:
<223> OTHER INFORMATION: recombinant antibody sequence

<400> SEQUENCE: 12

Asp Ala Ser Asp Leu Ala Ser
1               5

<210> SEQ ID NO 13
<211> LENGTH: 11
<212> TYPE: PRT
<213> ORGANISM: artificial sequence
<220> FEATURE:
<223> OTHER INFORMATION: recombinant antibody sequence

<400> SEQUENCE: 13

Ala Gly Gly Phe Ser Ser Ser Ser Asp Thr Ala
1               5                   10

<210> SEQ ID NO 14
<211> LENGTH: 10
<212> TYPE: PRT
<213> ORGANISM: artificial sequence
<220> FEATURE:
<223> OTHER INFORMATION: recombinant antibody sequence

<400> SEQUENCE: 14

Gly Phe Ser Leu Ser Ser Asn Ala Met Gly
1               5                   10

<210> SEQ ID NO 15
<211> LENGTH: 16
<212> TYPE: PRT
<213> ORGANISM: artificial sequence
<220> FEATURE:
<223> OTHER INFORMATION: recombinant antibody sequence

<400> SEQUENCE: 15

Ile Ile Ser Val Gly Gly Phe Thr Tyr Tyr Ala Ser Trp Ala Lys Gly
1               5                   10                  15

<210> SEQ ID NO 16
<211> LENGTH: 14
<212> TYPE: PRT
<213> ORGANISM: artificial sequence
```

```
<220> FEATURE:
<223> OTHER INFORMATION: recombinant antibody sequence

<400> SEQUENCE: 16

Arg Asp Arg His Gly Gly Asp Ser Ser Gly Ala Phe Tyr Leu
1               5                   10

<210> SEQ ID NO 17
<211> LENGTH: 11
<212> TYPE: PRT
<213> ORGANISM: artificial sequence
<220> FEATURE:
<223> OTHER INFORMATION: recombinant antibody sequence

<400> SEQUENCE: 17

Gln Ala Ser Gln Ile Ile Ser Ser Arg Ser Ala
1               5                   10

<210> SEQ ID NO 18
<211> LENGTH: 7
<212> TYPE: PRT
<213> ORGANISM: artificial sequence
<220> FEATURE:
<223> OTHER INFORMATION: recombinant antibody sequence

<400> SEQUENCE: 18

Gln Ala Ser Lys Leu Ala Ser
1               5

<210> SEQ ID NO 19
<211> LENGTH: 11
<212> TYPE: PRT
<213> ORGANISM: artificial sequence
<220> FEATURE:
<223> OTHER INFORMATION: recombinant antibody sequence

<400> SEQUENCE: 19

Gln Cys Thr Tyr Ile Asp Ser Asn Phe Gly Ala
1               5                   10

<210> SEQ ID NO 20
<211> LENGTH: 11
<212> TYPE: PRT
<213> ORGANISM: artificial sequence
<220> FEATURE:
<223> OTHER INFORMATION: recombinant antibody sequence

<400> SEQUENCE: 20

Gly Phe Ser Phe Ser Ser Ser Tyr Trp Ile Cys
1               5                   10

<210> SEQ ID NO 21
<211> LENGTH: 17
<212> TYPE: PRT
<213> ORGANISM: artificial sequence
<220> FEATURE:
<223> OTHER INFORMATION: recombinant antibody sequence

<400> SEQUENCE: 21

Cys Val Phe Thr Gly Asp Gly Thr Thr Tyr Tyr Ala Ser Trp Ala Lys
1               5                   10                  15

Gly
```

```
<210> SEQ ID NO 22
<211> LENGTH: 12
<212> TYPE: PRT
<213> ORGANISM: artificial sequence
<220> FEATURE:
<223> OTHER INFORMATION: recombinant antibody sequence

<400> SEQUENCE: 22

Arg Pro Val Ser Val Tyr Tyr Tyr Gly Met Asp Leu
1               5                   10
```